(12) United States Patent
Moulds et al.

(10) Patent No.: US 10,325,766 B2
(45) Date of Patent: Jun. 18, 2019

(54) METHOD OF OPTIMISING SPECTRAL DATA

(71) Applicant: Micromass UK Limited, Wilmslow (GB)

(72) Inventors: Richard Moulds, Stockport (GB); Keith Richardson, High Peak (GB); Jason Lee Wildgoose, Stockport (GB); Martin Raymond Green, Bowden (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/301,172

(22) PCT Filed: Apr. 1, 2015

(86) PCT No.: PCT/GB2015/051017
§ 371 (c)(1),
(2) Date: Sep. 30, 2016

(87) PCT Pub. No.: WO2015/150806
PCT Pub. Date: Oct. 8, 2015

(65) Prior Publication Data
US 2017/0011899 A1    Jan. 12, 2017

(30) Foreign Application Priority Data

Apr. 1, 2014 (EP) ..................................... 14163020
Apr. 1, 2014 (GB) .................................... 1405828.3

(51) Int. Cl.
*H01J 49/26* (2006.01)
*H01J 49/00* (2006.01)
(Continued)

(52) U.S. Cl.
CPC ........ *H01J 49/0036* (2013.01); *G01N 27/622* (2013.01); *H01J 49/0031* (2013.01); *H01J 49/0045* (2013.01); *H01J 49/40* (2013.01)

(58) Field of Classification Search
CPC ............... H01J 49/0031; H01J 49/0036; H01J 49/0045; G01N 27/622
See application file for complete search history.

(56) References Cited

U.S. PATENT DOCUMENTS 7,158,862 B2 * 1/2007 Liebler ............... H01J 49/0036
250/281
7,323,682 B2    1/2008 McCauley et al.
(Continued)

FOREIGN PATENT DOCUMENTS

WO    2011/058381    5/2011
WO    2012/175978    12/2012

OTHER PUBLICATIONS

Geiger et al., "Proteomics on an Orbitrap Benchtop Mass Spectrometer Using All-ion Fragmentation", Molecular & Cellular Proteomics, vol. 9, No. 10. p. 2252-2261, 2010.
(Continued)

*Primary Examiner* — Eliza W Osenbaugh-Stewar

(57) ABSTRACT

A method of mass spectrometry or ion mobility spectrometry is disclosed. The method comprises: providing a plurality of species of ions; analyzing the ions during a plurality of sequential acquisition periods so as to obtain spectral data relating to the ions; varying the value of an operational parameter of the spectrometer such that it has different values during the different acquisition periods, wherein the spectral data obtained for a given ion varies depending on the value of the operational parameter; storing the spectral data obtained during the different acquisition periods separately; selecting a target ion; and then interrogating the spectral data so as to identify a set of first acquisition periods
(Continued)

that include data corresponding to said target ion. Selecting spectral data from only a subset of the first acquisition periods allows the selection of the optimal spectral data for the target ion, while discarding less optimal data.

19 Claims, 6 Drawing Sheets

(51) Int. Cl.
  *G01N 27/62* (2006.01)
  *H01J 49/40* (2006.01)

(56) References Cited

U.S. PATENT DOCUMENTS

| | | |
|---|---|---|
| 7,595,485 B1 | 9/2009 | Sadygov et al. |
| 8,278,620 B2 | 10/2012 | Schwartz et al. |
| 8,373,115 B2 | 2/2013 | Geromanos et al. |
| 8,704,161 B2 | 4/2014 | Kawana |
| 8,921,773 B2 | 12/2014 | Geromanos et al. |
| 9,469,558 B2 | 2/2016 | Shiohama |
| 9,299,548 B2 | 3/2016 | Bonner et al. |
| 2010/0065733 A1 | 3/2010 | Bateman et al. |

OTHER PUBLICATIONS

Pavlic et al., "Combined use of ESI-QqTOF-MS and ESI-QqTOF-MS/MS with Mass-Spectral Library Search for Qualitative Analysis of Drugs", Anal Bioanal Chem, vol. 386, p. 69-82, 2006.

\* cited by examiner

--Prior Art--

METHOD OF OPTIMISING SPECTRAL DATA

CROSS REFERENCE TO RELATED APPLICATIONS

This application is the National Stage of International Application No. PCT/GB2015/051017, filed 1 Apr. 2015 which claims priority from and the benefit of United Kingdom patent application No. 1405828.3 filed on 1 Apr. 2014 and European patent application No. 14163020.2 filed on 1 Apr. 2014. The entire contents of these applications are incorporated herein by reference.

BACKGROUND TO THE PRESENT INVENTION

In mass spectrometry it is sometimes required to control an operational parameter of the instrument in order to optimise the acquisition of data from species of interest. However, it is often not possible to determine the optimal acquisition parameters for the species of interest in advance of an experiment. Also, different parameters may be optimal for different species of interest.

It is known to analyse ions and accumulate data whilst the value of an operational parameter, such as collision energy, is being ramped. This enables the operational parameter to be optimised for each of the species during a part of the acquisition period and hence the data obtained can be used to generate a spectrum having contributions from optimal values for each species. However, the operational parameter will not be optimised for any given species during much of the acquisition period and hence the spectrum necessarily includes significant contributions from non-optimal values.

For example, when using an analytical filter such as a quadruple mass filter in which a single species is transmitted at any one filter setting, instrument conditions may be optimised for each mass to charge ratio value independently. One example is the optimisation of DC potentials on a DC focussing element for best ion transmission in an atmospheric pressure ion source. In many cases there is a compromise of selecting between DC potentials that optimise ion focussing so that ion transmission is improved and DC potentials that cause ion fragmentation due to collisions with background gas. In some cases, this fragmentation may be desirable and in others it may reduce the transmission of a selected ion. Such a DC focussing element may be termed Source Fragmentation Voltage (SFV) or "Cone Voltage".

In contrast, a time of flight (TOF) instrument transmits the whole mass range at once, and so the SFV cannot be optimised by for every mass to charge ratio being analysed at the same time. The state of art is to either fix the SFV for an experiment or to scan the operational voltage over a range while acquiring multiple time of flight spectra and then average the resultant spectra. This leads to poorly optimised signals and for a given mass to charge ratio the SFV may give poor sensitivity and/or promote fragmentation of other masses, causing increased noise.

Although a couple of examples have been provided above, many other operational parameters would benefit from being optimised according to the nature of each spectral species. The current state of the art can only result in a best compromise value of the operational parameter for the species which are simultaneously analysed.

It is therefore desired to provide an improved method of mass spectrometry or ion mobility spectrometry, and an improved mass spectrometer.

SUMMARY OF THE PRESENT INVENTION

According to a first aspect the present invention provides a method of mass spectrometry or ion mobility spectrometry comprising:

providing a plurality of species of ions;

analysing the ions during a plurality of sequential acquisition periods so as to obtain spectral data relating to the ions;

varying the value of an operational parameter of the spectrometer such that it has different values during the different acquisition periods, wherein the spectral data obtained for a given ion varies depending on the value of the operational parameter;

storing the spectral data obtained during the different acquisition periods separately;

selecting or identifying a target ion; and then interrogating the spectral data so as to identify a set of first acquisition periods that include data corresponding to said target ion; and selecting spectral data obtained in only a subset of said first acquisition periods so as to obtain spectral data that is optimised for said target ion.

The operational parameter of the spectrometer has different values for different acquisition periods in the first set of acquisition periods. As such, the spectral data for the target ion differs in at least some of the different acquisition periods of said first set. Selecting spectral data from only a subset of these first acquisition periods therefore allows the selection of the optimal spectral data for the target ion (i.e. the best data of the data in the first set), whilst discarding less optimal data. For example, spectral data in acquisition periods of said first set that have higher signal to noise ratios may be selected, whilst spectral data in the other acquisition periods of said first set that have lower signal to noise ratios may be discarded.

EP 2639815 discloses a method of calibrating a triple quadrupole MS/MS device that involves determining the optimum peak of the product ions derived from a known precursor ion. The method selects a precursor ion and then subjects the precursor ion to a plurality of different scans, wherein the operational conditions of the spectrometer are varied between the different scans. The method then examines the spectra obtained from the scans and determines the optimum product ion peak. For example, the product ion peak that occurs most frequently in the different spectra may be considered to be the optimum product ion peak.

EP 2639815 differs from the present invention in that it does not select a target ion, and then interrogate the spectral data obtained during different acquisition periods so as to identify the acquisition periods that include data corresponding to said target ion (i.e. said first acquisition periods), and then select spectral data obtained in only a subset of these first acquisition periods so as to obtain spectral data that is optimised for said target ion. In contrast, EP'815 interrogates the spectral data first, before any target ion is selected. This is because EP'815 seeks to identify the most frequently occurring product ion in a set of spectral data, rather than optimising the spectral data for a particular target ion, as does the present invention.

The step of selecting spectral data obtained in only a subset of said first acquisition periods so as to obtain spectral data that is optimised for said target ion may comprise scoring or rating the spectral data in the acquisition periods of said first set according to at least one predefined criterion, and then selecting said first acquisition periods as the acquisition periods containing spectral data having a higher score or rating, and discarding the other acquisition periods of said first set that contain spectral data having a lower score or rating. Acquisition periods having a scoring or rating above a threshold value may be selected, and acquisition periods having a scoring or rating below the threshold value may be discarded. For example, spectral data may be scored or rated according to the intensity or signal to noise ratio of the spectral signal.)

The sequential acquisition periods may be performed on the same sample in a single experimental run; and/or may be performed immediately one after the other.

The acquisition periods are sequential and may be such that ions are substantially continually analysed throughout the plurality of sequential acquisition periods.

The method may be a method of time of flight mass spectrometry.

The method is particularly suited to a method of time of flight mass spectrometry since each acquisition period corresponds to a different operational parameter value and includes a full spectrum for all ions, thus enabling optimal spectral data to be obtained for each ion in at least one of the acquisition periods.

The method may be a method of orthogonal acceleration time of flight mass spectrometry.

In time of flight methods, the spectral data obtained in each of one or more of said acquisition periods may correspond to the spectral data obtained in a single time of flight separation. Alternatively, the spectral data obtained in each of one or more of said acquisition periods may correspond to the spectral data obtained in a plurality of, but not all of, the time of flight separations.

The present invention may employ analysers other than time of flight mass analysers.

Said plurality of species of ions may be provided from a sample and the spectral data obtained in said subset of said first acquisition periods may be used to identify or quantify an analyte in the sample, or an analyte derived from said sample.

The target ion may have a known physicochemical property value, and said step of interrogating the spectral data so as to identify the set of first acquisition periods may comprise interrogating the spectral data so as to identify a set of first acquisition periods that includes data corresponding to ions having said known physicochemical property value.

Said physicochemical property may be mass to charge ratio or ion mobility.

The target ion may have known values for more than one physicochemical property and these different physicochemical property values may be used to identify the set of first acquisition periods. For example, the target ion may have a known mass to charge ratio and a known ion mobility, both of which may be used to identify the set of first acquisition periods.

The method may comprise continuously scanning the value of the operational parameter across different values during the acquisition periods; or may comprise discontinuously stepping the value of the operational parameter between different values for the different acquisition periods.

The value of the operational parameter may be progressively increased with time and/or may be progressively decreased with time across the acquisition periods, regardless of whether the operational parameter value is scanned or stepped. The value of the operational parameter may be progressively increased with time and then progressively decreased with time over the acquisition periods, or vice versa.

The method may comprise varying the value of the operational parameter in a cyclical manner, wherein the value of the operational parameter is varied as a function of time in the same manner or pattern for each of the cycles.

Said set of first acquisition periods may include one or more acquisition periods from each of a plurality of different ones of said cycles.

Each cycle preferably spans more than one acquisition period.

The operational parameter may be substantially constant within each acquisition period. Alternatively, if the operational parameter value is being continuously scanned then some change in the parameter value will occur during each acquisition period, but such a change may be selected so as not to have a significant effect on the ions being analysed during that acquisition period.

As described above, the operational parameter is different for the different acquisition periods of the first set of acquisition periods. If the operational parameter has more than one value for each acquisition period, e.g. is scanned or stepped through a range of values during each acquisition period, then the ranges of values may be different for different acquisition periods. The ranges of values for the different acquisition periods may be non-overlapping.

Ions of the same ion species may be analysed in a plurality of different ones of said acquisition periods such that different spectral data is obtained for said same ion species in the different acquisition periods.

The step of selecting spectral data may comprise comparing mass and/or mobility spectral data of at least one of the same ion species recorded in different acquisition periods, and selecting spectral data from at least one of said different acquisition periods for further processing based on this comparison. Alternatively, the step of selecting spectral data may comprises comparing spectral data obtained in different acquisition periods and that has been obtained by mass or ion-mobility analysing at least one of the same ion species, and selecting spectral data for further processing based on the comparison.

A plurality of species of ions may be analysed during each of a plurality of the acquisition periods.

For example, all of the species of ions may be analysed during each of all of the acquisition periods.

Ions of the same ion species are analysed in a plurality of different ones of said acquisition periods such that different spectral data is obtained for said same ion species in the different acquisition periods. Ions of the same species may be analysed during all of the acquisition periods, or in only some of the acquisition periods. The spectral data obtained for a given species of ion may be different in each of the acquisition periods. However, it is contemplated that the spectral data obtained for a given species of ion may be the same in some of the acquisition periods. For example, the signal for an ion species may be optimised at two or more different operational parameter values.

Ions of a plurality of said ion species, or ions of all of said ion species, may be analysed in all of the acquisition periods. Alternatively, ions of a plurality of said species may be analysed in only some of the acquisition periods.

Therefore, the method may comprise varying the operational parameter such that each species of ions is subjected to different operational parameter values in different acquisition periods, or is subjected to different ranges of operational parameter values in different acquisition periods. This method has the advantage that spectral data may be obtained for each species of ions at different operational parameter values and it is therefore not required to determine the optimum operational parameter for the species of ion in advance of the experiment. Rather, the spectral data can be interrogated in order to determine which of the operational parameter values provides optimum spectral data for the species of ion in question.

The method may comprise combining/integrating, summing or averaging spectral data obtained in said first subset of acquisition periods to form one or more combined, summed or averaged data set.

The method may comprise only combining/integrating, summing or averaging spectral data obtained in different acquisition periods that correspond to the same operational parameter value or that correspond to the same range of operational parameter values.

The method may comprise producing different spectra for said different species, wherein the different spectra are produced using spectral data obtained in different subsets of said acquisition periods.

Alternatively, the method may comprise producing different spectra for the same species, wherein the different spectra are produced using spectral data obtained in different subsets of said acquisition periods.

The method may comprise selecting a desired operational parameter value or range of values, and extracting spectral data in a, or the, acquisition period(s) corresponding to the desired operational parameter value or values.

The method may comprise filtering spectral data obtained in the acquisition periods according to a known physicochemical property value or values of the target ion, and then extracting or only retaining spectral data for ions having this desired physicochemical property value or values.

The value(s) of the optimum operational parameter or expected range of the optimum operational parameter may be known or predetermined for at least some of the species of ions, such as the target ion. It may therefore be desired to select spectral data for these ions that has been obtained using an operational parameter value that is (or values that are) at or close to the optimum value(s). For example, the spectral data may be filtered according to the mass to charge ratio and it may be desired to select or extract spectral data for one or more desired mass to charge ratios, or a range of desired mass to charge ratios, wherein that spectral data is from one or more acquisition periods that represent the optimum operational parameter(s) for the desired mass to charge ratio(s). The data may therefore be filtered based on prior knowledge about the optimum operational parameter.

The method may comprise interrogating the spectral data obtained in the acquisition periods based on one or more predefined criterion, and selecting or combining spectral data from one or more subset of the acquisition periods to obtain spectral data that is optimised for said one or more predefined criterion.

Said step of selecting spectral data obtained in only a subset of said first acquisition periods so as to obtain spectral data that is optimised for said target ion may comprise: selecting spectral data from acquisition periods of said first set that have higher signal to noise ratios, and discarding or ignoring spectral data in the other acquisition periods of said first set that have lower signal to noise ratios; and/or selecting spectral data from acquisition periods of said first set that have higher signal intensity, and discarding or ignoring spectral data in the other acquisition periods of said first set that have lower signal intensity.

The methods described herein, particularly the data processing steps for selecting, combining or extracting spectral data, may be performed automatically.

The step of providing the plurality of species of ions may comprise providing said plurality of species of ions separated according to a physicochemical property. The method may comprise repeatedly varying the operational parameter between at least two values such that each of the different separated species of ions is subjected to said at least two operational parameter values, and the acquisition periods may be selected such that spectral data obtained at each of said at least two values is recorded separately.

The physicochemical property may be liquid chromatography elution time, mass to charge ratio, ion mobility or any other physicochemical property The operational parameter value may be stepped between different values, and each time that the operational parameter is stepped to a new value may correspond to a new acquisition period. Alternatively, the value of the operational parameter may be substantially continuously scanned with time such that different operational parameter values correspond to different acquisition periods.

The value of the operational parameter may be stepped or scanned between different values in each cycle of a plurality of cycles. The operational parameter values may be the same or different in different cycles. In this method the optimum parameter value may be known for at least some of the species of ions, but the values of the physicochemical properties of the species may not be known. Varying the operational parameter between values that are substantially at the known optimum values for the species ensures that each species will be subjected to an operational parameter value that is at or close to its optimum value during at least some of the acquisition periods.

The optimum parameter value may be known or predetermined for at least two of the species of ions, and said at least two operational parameter values may be substantially the optimum parameter values for said at least two species such that each species will be subjected to an operational parameter value that is substantially at its optimum value during at least some of the acquisition periods.

In this method, said at least two of the species of ions may be said target ions.

The operational parameter value of the spectrometer may be varied such that each species of ions that is analysed experiences an operational parameter value that is at or close to its optimum value. If multiple species of ions have similar optimum values then the operational parameter value of the spectrometer may remain the same during the analysis of these ions.

The method may comprise repeatedly cycling the operational parameter value between different values, wherein each cycle comprises at least two different values, and wherein the values of the operational parameter in the cycles are varied as a function of the physicochemical property values of the species being subjected to the operational parameter.

For example, the species may be separated by chromatography and the operational parameter values that are cycled between may vary as a function of elution time.

The present invention is a method of mass spectrometry or ion mobility spectrometry, which therefore analyses (e.g. separates) ions according to their mass to charge ratios or ion mobilities during said acquisition periods. According to the above-described method, the operational parameter value is varied with respect to a physicochemical property other than mass to charge ratio or ion mobility, i.e. with respect to chromatography elution time. This separation with respect to the different physicochemical property is slower than the analysis (i.e. separation) by mass to charge ratio or ion mobility. In the above example of separation by chromatography, the separation is an orthogonal separation technique to the mass analysis or ion mobility analysis. However, the separation with respect to the different physicochemical property may be with respect to a physicochemical property other than chromatography elution time. For example, ions may be separated according to their mass to charge ratio and then these ions may be subjected to the operational parameter, which is varied as a function of the mass to charge ratio before being analysed during the acquisition periods. This may be achieved, for example, by using a mass selective ion trap to release ions relatively slowly in mass order and then the operational parameter may be varied as a function of mass to charge ratio. The operational parameter that is varied may be the collision energy of the ions. The resulting ions are then analysed during the acquisition periods, e.g. via a TOF mass analyser. This may be used to obtain a collisional energy potential verses fragment ion appearance plot for each mass released from the ion trap.

The method may comprise generating a chromatogram using the selected spectral data resulting from the steps described herein; and/or may comprise identifying one or more ions using the selected data described herein or said chromatogram.

The operational parameter value that is varied may be selected from one of: a potential difference used to accelerate the ions; a collision energy with which the ions are caused to collide with a gas or surface; a fragmentation energy for fragmenting the ions;

a gain of a detector for detecting the ions; an ion beam attenuation; a reaction time with which the ions are reacted with reactants (e.g. ETD reaction time); an amount of attenuation or filtering of the ions; and a source ionisation efficiency or sensitivity or ionisation energy.

For example, an ion beam may be attenuated and the present invention may be used to select spectral data corresponding to the optimal transmission rate for each ion species of interest. This technique may be used to extract spectral data obtained when the detector is not saturated by a high arrival rate of ions. This optimal spectral data may be integrated, e.g. in order to form an optimal chromatogram. This would enable more accurate measurements to be made from the optimal data, such as measurements of ion mass or mobility.

Another example is where the operational parameter is the fragmentation energy with which ions are fragmented. Spectral data for acquisition periods in which the fragmentation energy is set to be relatively high may be combined in order to form high energy spectral data. This data may be compared to a database of fragment ions or fragment patterns in order to identify the ions that have fragmented.

The step of varying the operational parameter may not selectively transmit or filter ions, or restrict the population of ions in the spectrometer.

The spectral data described herein may be mass spectral data or ion mobility spectral data.

The operational parameter value is scanned or stepped between different values as the species of ions are analysed. In methods where the operational parameter value is stepped, a different acquisition period may be provided for each different value of the operational parameter such that spectral data obtained at different parameter values are stored separately. The method may step between x operational parameter values, wherein x may be $\geq 2$, $\geq 3$, $\geq 4$, $\geq 5$, $\geq 10$, $\geq 15$ or $\geq 20$. If the parameter value is stepped in a cyclically pattern, then x acquisition periods may be provided per scan cycle.

In methods where the operational parameter value is scanned, e.g. continuously scanned, x acquisition periods may be provided per scan, wherein x may be $\geq 2$, $\geq 3$, $\geq 4$, $\geq 5$, $\geq 10$, $\geq 15$ or $\geq 20$. If the parameter value is scanned cyclically, then x acquisition periods may be provided per scan cycle.

The method of mass spectrometry may not be a method of $MS^e$ spectrometry and may not be a method wherein ions are alternated between different collision energies.

The step of storing the spectral data obtained during the different acquisition periods separately may comprise storing data in more than two separate data stores. Each data store may be associated with the acquisition period(s) that the data stored therein is related to. Data from different acquisition periods may be stored in $\geq 3$, $\geq 4$, $\geq 5$, $\geq 6$, $\geq 7$, $\geq 8$, $\geq 9$ or $\geq 10$ separate data stores respectively. Data from each acquisition period may be stored separately in its own data store.

The operational parameter of the present invention may be varied between $\geq 2$ non-zero values, possibly between 3, $\geq 4$, $\geq 5$, $\geq 6$, $\geq 7$, $\geq 8$, $\geq 9$ or $\geq 10$ different non-zero values. The step of selecting spectral data may select data which maximises one of, or a combination of; signal intensity, signal to noise ratio, mass measurement accuracy and/or quantitative accuracy for a given ion (e.g. the target ion).

The operational parameter may be ion beam attenuation, and the method may comprise selecting spectral data obtained at known values of ion beam attenuation, determining the intensity of the spectral data, and using said intensity to estimate the total intensity of the spectral data over all of the operational values or to rescale the intensities of the data to correspond to those of an unattenuated beam.

The operational parameter may not substantially select or reject specific analyte ions from the ion population; and/or the operational parameter may be varied in a manner whereby it affects all of the ions that are analysed.

It will be appreciated that the method may select more than one target ion, so as to obtain spectral data that is optimised for more than one target ion.

The step of varying the value of the operational parameter may be performed after the plurality of ions have been generated and so as to affect the ions.

The method may comprise further processing the selected spectral data.

The method may not be a method of calibrating an instrument.

The method may comprise ionising a sample so as to provide said step of providing a plurality of species of ions. The composition of the sample may only be partially known or may be unknown.

It is also contemplated that the above-described methods may not be limited to including the steps of: selecting or identifying a target ion; and then interrogating the spectral data so as to identify a set of first acquisition periods that include data corresponding to said target ion; and selecting spectral data obtained in only a subset of said first acquisition periods so as to obtain spectral data that is optimised for said target ion.

Accordingly, from a second aspect, the present invention provides a method of mass spectrometry or ion mobility spectrometry comprising:

providing a plurality of species of ions;

analysing the ions during a plurality of sequential acquisition periods so as to obtain spectral data relating to the ions;

varying the value of an operational parameter of the spectrometer such that it has different values during the different acquisition periods, wherein the spectral data obtained for a given ion varies depending on the value of the operational parameter;

storing the spectral data obtained during the different acquisition periods separately; and selecting only spectral data obtained in one or more subset of said acquisition periods for further processing.

The method according to this aspect may have any one, or any combination, of the features described above in relation to the first aspect of the present invention as being preferred or optional.

According to a third aspect, the present invention provides a method of mass spectrometry or ion mobility spectrometry comprising:

(i) providing a plurality of species of ions;

(ii) analysing the ions during a plurality of sequential acquisition periods so as to obtain spectral data relating to the ions;

(iii) varying the value of an operational parameter of the spectrometer such that it has different values during the different acquisition periods, wherein the spectral data obtained for a given ion varies depending on the value of the operational parameter;

(iv) specifying one or more subsets of said acquisition periods and/or specifying one or more subsets of said spectral data obtained; and (v) storing only the data obtained in said one or more subsets of said acquisition periods or storing only said one or more subsets of said spectral data obtained, and discarding other data.

This aspect may comprise specifying the acquisition periods or data that is desired to be kept and then only acquiring such data or only storing such data to disc. This is may be useful, for example, when it is know in advance which region of the parameter space is desired to be kept or interrogated. This enables saving of storage space. In the example where the analyser is a TOF analyser, this technique allows one to only sum ion arrival events in the regions of m/z and parameter value specified.

The method according to this aspect may have any one, or any combination of any two or more, of the features described above in relation to the first aspect of the present invention.

According to a fourth aspect, the present invention provides a method of mass spectrometry or ion mobility spectrometry comprising:

providing a plurality of species of ions;

analysing the ions during a plurality of sequential acquisition periods so as to obtain spectral data relating to the ions;

varying the value of an operational parameter of the spectrometer such that it has different values during the different acquisition periods, wherein the spectral data obtained for a given ion varies depending on the value of the operational parameter;

associating the spectral data obtained in each acquisition period with its respective operational parameter value(s) so as to form associated data for each acquisition period;

providing a database of analytes, wherein for each analyte the database includes spectral data obtained at a plurality of said operational parameter values, wherein the spectral data is associated with the operational parameter value(s) that it was obtained at;

searching said database using said associated data;

determining an analyte in the database that has spectral data at a plurality of operational parameter values which matches the associated data obtained at substantially the same operational parameter values.

The spectral data being compared may be in the form of images, such as graphs. For example, the spectral data may be a graph of data points, wherein each data point graphically depicts a mass to charge ratio or ion mobility of an ion, and the operational parameter value at which it was acquired. The spectral data obtained is preferably in the same format as the spectral data in the database so that the comparison can be made.

The spectral data obtained is preferably via mass analysis or ion mobility analysis.

The step of analysing the ions preferably comprises mass analysing the ions or analysing the ion mobility of the ions. The step of analysing the ions may comprise fragmenting the ions and then analysing the mass or ion mobility of the resulting fragment ions.

The above technique may be used to fingerprint species of ions. For example, the operational parameter may be the fragmentation energy of parent ions and different fragment ions may be generated for the same parent ion at different fragmentation energies, due to the energetics of the bonds. The resulting fragmentation pattern may be characteristic of a particular compound and so it can be used to library search or pattern match so as to identify the parent ion.

It is also contemplated that the spectral data obtained from the analysis and the spectral data in the database may be correlated with one or more other parameters for use in matching the data sets. For example, the other parameter may be liquid chromatography retention time or retention time of some other separation device.

In some cases, the value or values of the operational parameter selected for a particular ion species are characteristic of the ion species. For example, a particular product ion species formed by dissociation of a specific precursor species will have optimum intensity over a characteristic range of fragmentation energies. This information may be associated with the data selected for each ion species and used as an additional identification criterion by comparing to a data base of known energy ranges for this transition.

According to the method described herein, the operational parameter preferably does not substantially select or reject specific analyte ions from the ion population; and/or the operational parameter is preferably varied in a manner whereby it affects all of the ions that are analysed.

The present invention also provides a mass or ion mobility spectrometer arranged and configured to perform any one or combination of the methods described herein.

Accordingly, the present invention provides a mass or ion mobility spectrometer comprising:

an ion analyser configured to analyse ions during a plurality of sequential acquisition periods so as to obtain spectral data relating to the ions; and a controller configured to:

vary the value of an operational parameter of the spectrometer such that it has different values during the different acquisition periods and such that the spectral data obtained for a given ion varies depending on the value of the operational parameter;

store the spectral data obtained during the different acquisition periods separately;

interrogate the spectral data so as to identify a set of first acquisition periods that include data corresponding to a selected target ion; and select spectral data obtained in only a subset of said first acquisition periods so as to obtain spectral data that is optimised for said target ion.

The present invention provides a mass or ion mobility spectrometer comprising: an ion analyser configured to analyse ions during a plurality of sequential acquisition periods so as to obtain spectral data relating to the ions; and a controller configured to:

vary the value of an operational parameter of the spectrometer such that it has different values during the different acquisition periods and such that the spectral data obtained for a given ion varies depending on the value of the operational parameter;

store the spectral data obtained during the different acquisition periods separately; and select only spectral data obtained in one or more subset of said acquisition periods for further processing.

The present invention provides a mass or ion mobility spectrometer comprising:

an ion analyser configured to analyse ions during a plurality of sequential acquisition periods so as to obtain spectral data relating to the ions; and a controller configured to:

vary the value of an operational parameter of the spectrometer such that it has different values during the different acquisition periods and such that the spectral data obtained for a given ion varies depending on the value of the operational parameter; and store only the data obtained in one or more subsets of said acquisition periods or store only the one or more subsets of said spectral data obtained, and discarding other data.

The present invention provides a mass or ion mobility spectrometer comprising:

an ion analyser configured to analyse ions during a plurality of sequential acquisition periods so as to obtain spectral data relating to the ions; and a controller configured to: vary the value of an operational parameter of the spectrometer such that it has different values during the different acquisition periods and such that the spectral data obtained for a given ion varies depending on the value of the operational parameter; and associate the spectral data obtained in each acquisition period with its respective operational parameter value(s) so as to form associated data for each acquisition period;

a database of analytes, wherein for each analyte the database includes spectral data obtained at a plurality of said operational parameter values, wherein the spectral data is associated with the operational parameter value(s) that it was obtained at; and wherein the controller is configured to:

search said database using said associated data; and determine an analyte in the database that has spectral data at a plurality of operational parameter values which matches the associated data obtained at substantially the same operational parameter values.

The spectrometer may comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The spectrometer may comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The mass spectrometer may comprise a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide is preferably maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

As the present invention stores the spectral data in separate "channels" that relate to different operational parameter values, data from only some of the channels can be selected in order to obtain the optimum spectral data for a given criterion. This can be used to form improved spectral and/or chromatographic data and hence may lead to, for example, improved sensitivity, selectivity or identification of ions.

The present invention may be used to generate or select spectral data that is optimised for the different ions being analysed. This provides improved spectral data that may be used, for example, in order to provide improved measurements of mass, ion mobility, spectral peak intensity, spectral peak width, retention time or isotope ratio etc. As the spectral data is optimised by varying the operational parameter it may be used to improve the sensitivity of the instrument.

For example, the spectral data may be interrogated to obtain only data that has an improved signal to noise ratio (e.g. in ESI-TOF instruments).

The method may improve the ease of use of the spectrometer. For example, there is no requirement for the user to know what is the optimum operational parameter value prior to running the analysis.

The method may increase specificity, e.g. by enabling the operational parameter profile of a compound to be plotted or by aiding separation of co-eluting peaks through post acquisition processing.

The method may improve identification of compounds by acquiring high energy data and low energy data at the same time.

As described earlier, a plurality of analytes may elute from a separator (e.g. liquid chromatography separator) over respective elution time periods (e.g. LC peaks). The analytes may then be ionised so as to form said plurality of species of ions, and a plurality of said acquisition periods may be performed during the elution time period for each analyte (e.g. LC peak) such that ions of, or derived from, each analyte are analysed in a plurality of said acquisition periods. The method may vary the value of the operational parameter in a cyclical manner for a plurality of cycles during each elution time period (e.g. during each LC peak). The method may then determine which acquisition period(s) in each cycle gives the best data for a particular elution time period (e.g. LC peak). The spectral data in these acquisition periods may then be summed. This may be used to reduce the spectral data for each elution time period to a single spectrum that can be reconstructed as a mass or ion mobility chromatogram. The chromatogram may then be peak detected to give a final intensity and/or mass to charge ratio or ion mobility value for the analyte.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENT

In order to help understand the present invention, a single quadrupole MS experiment according to the prior art will now be described. According to the experiment, each compound of interest being investigated has an associated parent ion mass to charge ratio and an optimum Source Fragmentation Voltage (SFV) or "Cone Voltage". It is therefore desirable to provide a different SFV for each different compound of interest. This may be achieved by stepping the value of the SFV between different values as the different ions pass through the instrument, such that the different ions are subjected to their optimum SFV.

Figure 1A:
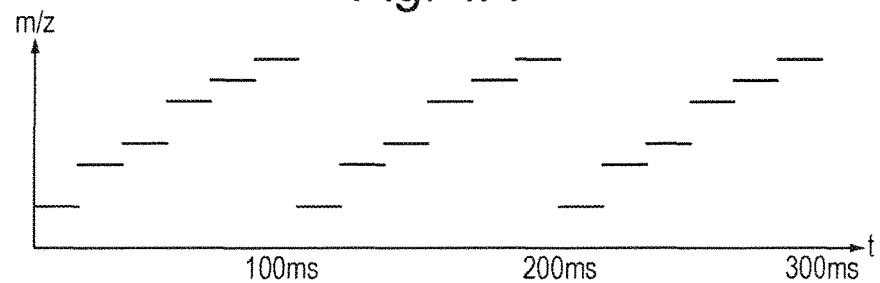
FIGS. 1A and 1B show a prior art technique for varying the SFV as a function of time.
Figure 1B:
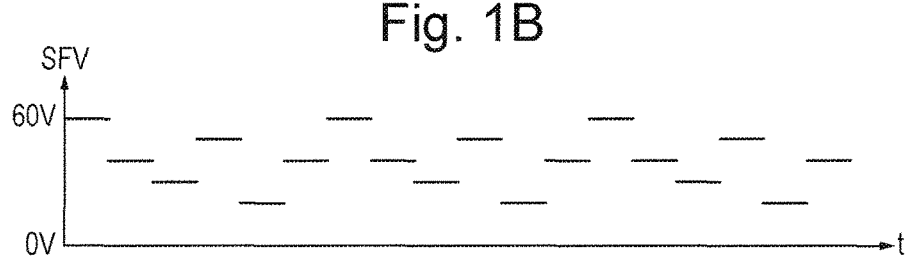

FIG. 1A and FIG. 1B show an example of how the SFV values and mass to charge ratios of the ions may vary as a function of time. FIG. 1A shows the mass to charge ratios of the ions that are transmitted through a quadrupole mass filter and subjected to the SFV as a function of time. It can be seen that six different ions of progressively increasing mass to charge ratio are sequentially transmitted during a period of 100 ms and that this cycle is repeated. Three cycles are shown in the graph. FIG. 1B shows how the SFV is stepped between different values at different times so that the SFV is optimised for each type of ion. This technique provides optimum sensitivity for the instrument. However, the technique requires advance knowledge of the optimum SFV for each ion. Furthermore, such a technique is less useful for instruments that analyse a range of different ions at the same time. For example, a time of flight (TOF) instrument acquires a whole mass range of ions at once, whereas the above technique cannot optimise the SFV for all of these different ions at the same time.

Figure 2A:
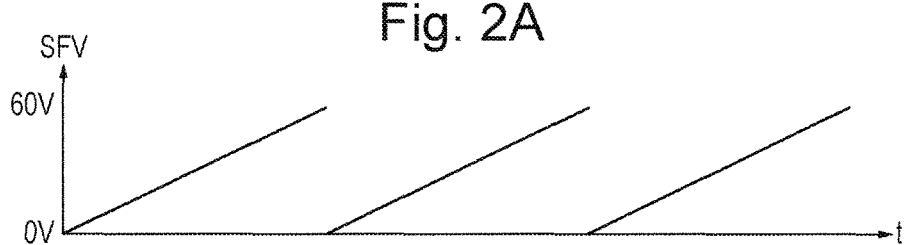
FIGS. 2A and 2B show another prior art technique for varying the SFV as a function of time.
Figure 2B:
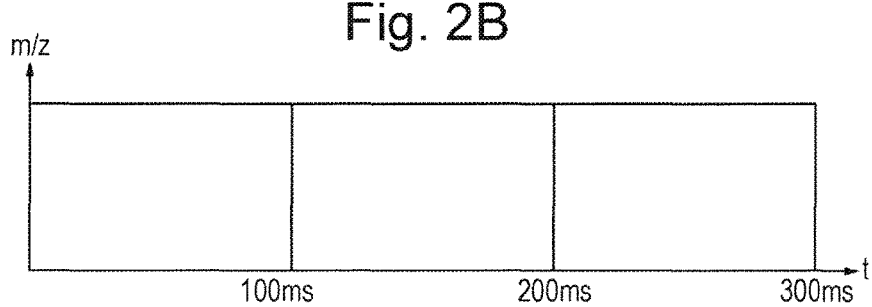

FIGS. 2A and 2B illustrate a prior art method for overcoming the above problem. FIG. 2A shows an example of how the SFV values vary as a function of time in an orthogonal TOF instrument. FIG. 2B shows that all ions having mass to charge ratios below the horizontal line are analysed at any given time. As seen from FIG. 2A, the SFV voltage is swept in a progressively increasing manner in each cycle, whilst individual time of flight spectra from each TOF separation are accumulated into a final histogrammed spectrum over the 100 ms time period. As the SFV voltage is varied with time, it is optimised for each of the ions over a portion of the TOF pulses. The instrument therefore has a good sensitivity for each of the different ions over a proportion of the pushes. For example, if the SFV is ramped between 20 V and 80 V, and the sensitivity for a particular compound is constant and optimum between 40V and 60V, and is zero for values outside this range, the effective duty cycle would be in excess of 33%. This would compare favourably with the example in FIG. 1, which has a duty cycle for each of the six different ions of 16%.

However, this method also has disadvantages. If the SFV is relatively high, then any high mass parent ions may be fragmented into (typically for singly charged ions) lower mass fragment ions. These fragment ions lead to many peaks at lower masses in the mass spectrum, which may interfere with the peaks of parent ions of similar masses to the fragment ions. As a result, subsequently extracted chromatograms will likely be far noisier than would be the case for an optimised SFV. This will be appreciated from FIGS. 3A to 3C.

Figure 3A:
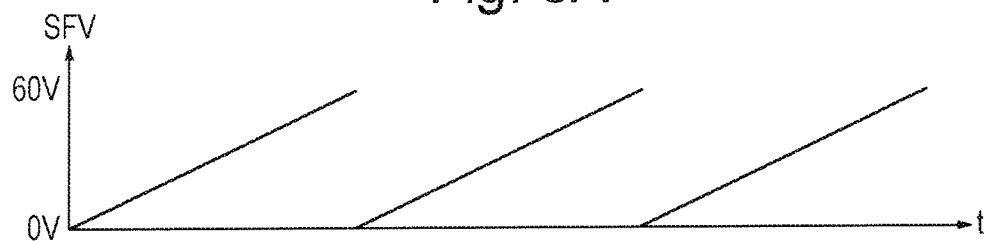
FIGS. 3A-3C show the effect of the SFV on the spectral data obtained.
Figure 3B:
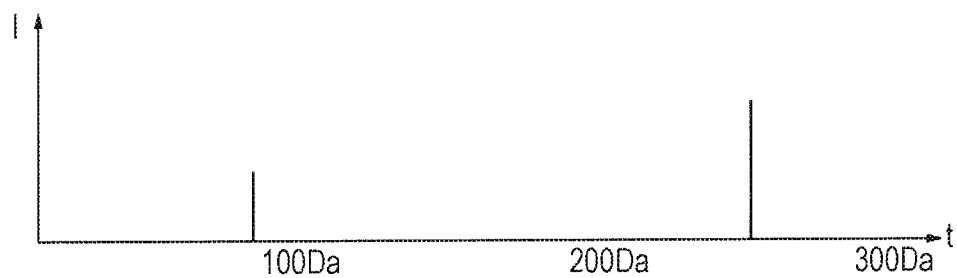
Figure 3C:
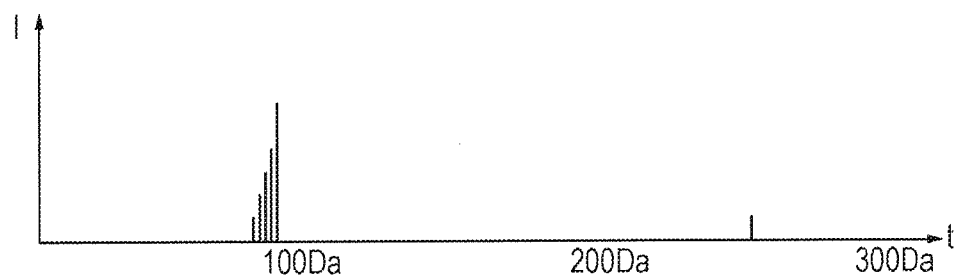

FIG. 3A corresponds to FIG. 2A and shows an example of how the SFV values vary as a function of time in a TOF instrument. FIG. 3B shows the mass spectrum obtained for SFV values in the range of 10-20 V. At this relatively low range of SFV values, a parent ion of an analyte can be observed at a mass under 100 Da and a parent ion of a co-eluting contaminant can be observed around 250 Da. FIG. 3C shows the mass spectrum obtained for SFV values in the range of 40-60 V. At this relatively high range of SFV values, peaks are still present corresponding to the two parent ions shown in FIG. 3B. However, the signal for the high mass parent ion is reduced because many of these ions have been fragmented at the high SFV values. Consequently, FIG. 3C includes many new peaks around the low mass parent ion, wherein the new peaks correspond to the fragment ions of the high mass parent ion. It will therefore be appreciated that the relatively high SFV values may generate fragment ions that obscure the signals of lower mass parent ions.

Figure 4A:
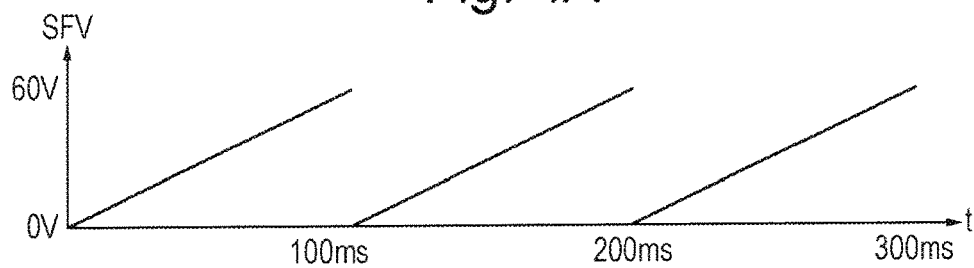
FIGS. 4A and 4B show a preferred embodiment of the present invention in which the SFV is progressively increased in each cycle.
Figure 4B:
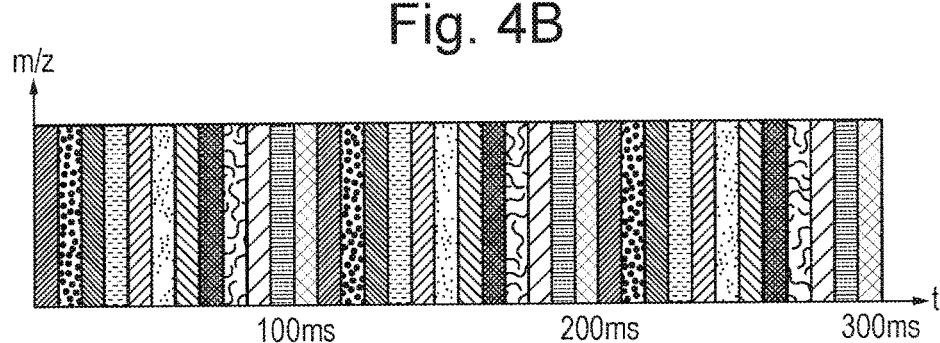

FIGS. 4A and 4B show a preferred embodiment of the present invention. According to this embodiment, the SFV values are scanned in the same manner as described above in relation to FIGS. 2A and 3A. FIG. 4B shows that all ions having mass to charge ratios below the horizontal line are analysed at any given time, in a similar manner to FIG. 2B. However, the preferred embodiment differs in that rather than combining TOF data over the entire duration of the SFV ramp to produce a single spectrum, many separate spectra are acquired during the period of the SFV ramp. Each of these spectra will be comprised of the summation of fewer individual time of flight data sets than in the single spectrum produced by the method of FIG. 2. In some cases each of the spectra of the preferred embodiment will be from an individual time of flight separation. This is represented by the bars of different shading in FIG. 4B. As can be seen from FIG. 4B, for each scan cycle of the SFV, there are 12 data acquisition periods that are represented by bars of different shading. Data acquired during the period represented by the first bar in each SFV scan represents ions experiencing low SFV values. Data acquired during the period represented by the second bar in each SFV scan represents ions experiencing higher SFV values. The SFV values become progressively higher for the 12 acquisition periods in any given SFV scan. This has the advantage described in relation to FIGS. 2A and 2B, that by scanning the SFV the SFV is optimised for each of the different ions over a portion of the cycle.

As the data from the different acquisition periods in each SFV scan are stored separately, a separate spectrum and/or chromatographic point can be extracted for each acquisition period which contains peaks generated with a small range of SFV values. For example, the data acquired during the first acquisition period may be extracted to produce a spectrum and/or chromatographic point that is generated using a small range of low SFV values. These SFV values will be optimised for certain ions within the data. Furthermore, the low SFV values will generate little, if any, fragmentation and so the spectrum will contain few, if any, fragment ion peaks. As such, fragment ion peaks from other precursor ions will not contribute significant noise or mass interference in the vicinity of the parent ion peaks. Conversely, data acquired during a later acquisition period, such as the last acquisition period in a scan, may be extracted to produce a spectrum and/or chromatographic point that is generated using a small range of high SFV values. These SFV values will be optimised for certain ions within the data, but such a spectrum may include peaks of fragment ions that are generated by the high SFV values.

Data from the corresponding acquisition periods in each scan cycle may be combined. For example, data obtained in the first acquisition period of each scan cycle may be combined to form a composite set of data for the first acquisition periods. A composite chromatogram may be formed from such combined data. Data from a plurality, or several, acquisition periods during each cycle of the SFV may be combined.

By varying the SFV and acquiring data in the manner described, the method enables the ion signal to be optimised for all ions without requiring predetermined knowledge of the optimum SFV for each ion and without having to specifically tune the SFV to the compound of interest.

Although FIG. 4 has been described in relation to progressively scanning the SFV values, it is also contemplated that the method may step between different SFV values during the different acquisition periods.

Figure 5A:
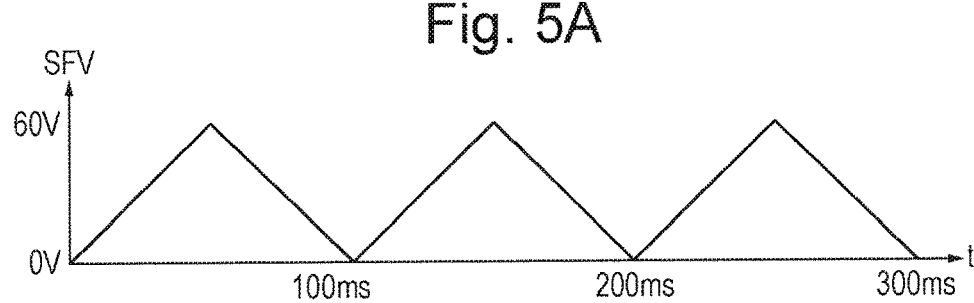
FIGS. 5A and 5B show a preferred embodiment of the present invention in which the SFV is progressively increased and then decreased in each cycle.
Figure 5B:
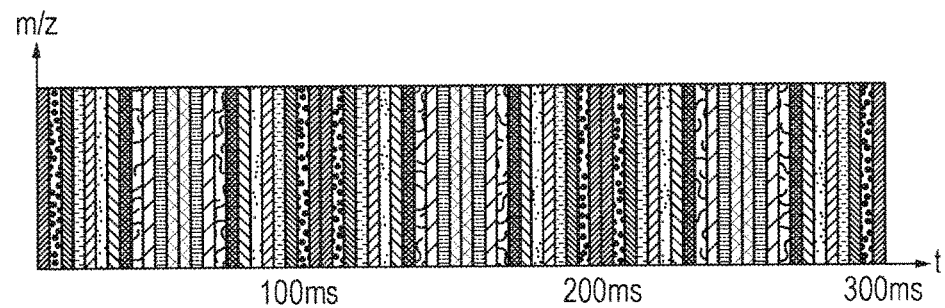

FIGS. 5A and 5B show a modification of the embodiment described in relation to FIGS. 4A and 4B. According to this embodiment the SFV is ramped up and then back down within each scan cycle. Accordingly, as can be seen from FIG. 5B, for each scan cycle of the SFV there are 24 data acquisition periods that are represented by bars of different colour. The SFV values become progressively higher for the first 12 acquisition periods in any given SFV scan and then become progressively lower for the next 12 acquisition periods in the scan cycle. Data from the two acquisition periods corresponding to the same range of SFV values in any given scan cycle may be combined. For example, data obtained in the first and last acquisition periods of any given scan cycle may be combined to form a composite set of data for these acquisition periods. A composite chromatogram may be formed from such combined data. Alternatively, or additionally, data obtained in acquisitions periods of different scan cycles that correspond to the same range of SFV values may be combined and a composite chromatogram may be formed from the resulting data.

The bidirectional ramping of the SFV may be used to reduce spectral skewing, as described in PCT/GB2012/051449. Typically, applying a low SFV results in spectral data that favours high m/z ions. Conversely, applying a high SFV results in spectral data that favours low m/z ions. Accordingly, scanning the SFV values may cause spectral skewing. However, by scanning the SFV values from low to high and then back to low again, the data will have reduced spectral skew. Spectral skewing occurs if the intensity of the signal for the analytes in the ion population is increasing or decreasing during the period over which the SFV is being changed.

Although FIG. 5 has been described in relation to progressively scanning the SFV values, it is also contemplated that the method may step between different SFV values during the different acquisition periods.

According to one embodiment, a plurality of ions of different mass to charge ratios are provided and are separated according to a physicochemical property prior to being subjected to the SFV. For example, the ions may be separated by liquid chromatography, mass to charge ratio or by ion mobility. The SFV may be varied by being progressively scanned or stepped whilst the separated ions pass through the SFV region. The SFV may be varied in a plurality of cycles as the ions pass through the SFV region, preferably at a rate such that each type of ion passing through the SFV region is subjected to all of, or the majority of, the SFV cycle. The ions are mass analysed during a plurality of data acquisition periods, wherein the data obtained during each acquisition period is stored separately and is correlated to a predetermined SFV value or range of SF values. Data in acquisition periods corresponding to the same SFV value or range of values may be combined.

A user may select data that has been acquired in one or more acquisition period that represents a given SFV value or a given range of SFV values. The data may then be displayed, for example, in the form of a chromatogram. The user may also specify a desired value of the physicochemical property (e.g. m/z value) or a desired range of values of the physicochemical property that the data is required for. If the value(s) of the physicochemical property and optimum SFV are known for the compound(s) of interest, then a computer system may be used to automatically select acquired data corresponding to these parameters. This data may then be used to produce a simplified chromatogram, i.e. a chromatogram that does not include data obtained in other acquisition periods. The computer may have access to a database that is populated by the physicochemical property values of ions and their corresponding optimum SFV values. The above techniques may be performed in real time processing.

The method may perform a number of post-processing techniques. For example, a user may enter a value or range of values for a physicochemical property of interest (e.g. m/z) and the data system may extract data for these values at a given SFV value or range of values and then generate a chromatogram using this data. The system may repeat this process iteratively for different SFV values or ranges of SFV values and then determine the chromatogram that provides the best signal to noise ratio. This process may result in more than one "recommended" extracted chromatogram. For example, in an LC experiment a m/z of 609 may produce a strong peak at 1 minute with an SFV range of 40-80 V and may produce another strong peak at 1.5 minutes with an SFV range of 20-50 V. Note that multi-dimensional peak detection algorithms to be applied as an alternative to iterative methods.

The SFV can be plotted as an extra dimension to the spectral information in a m/z, SFV, intensity plot. This would allow clear viewing and multi-dimensional peak detection algorithms to be applied.

The method may be used to determine and/or mark a peak with the optimum SFV range for that ion. For example, the optimum SFV range may be determined to be the range of SFV values within which the sensitivity is at or above x % of the maximum sensitivity. The value of x may be selected and may be, for example, 50. This technique could be used to increase specificity.

It is also contemplated that the invention could be used in a technique that is similar to an MS$^e$ technique. Conventional MSE methods separate the different species, e.g. by chromatography, and then transmit the ions to a device that is repeatedly alternated between a high fragmentation mode in which the ions are fragmented and a low fragmentation mode wherein the ions are substantially not fragmented. The resulting ions are analysed and the spectral data for the precursor ions obtained in the low fragmentation mode may be correlated to their fragment ions obtained in the high fragmentation mode by matching their elution times. According to a preferred embodiment of the present invention, the operational parameter is the collision energy of the ions and the collision energy is varied between more than two values (i.e. many collision energy values) so as to create profile information of the destruction of each parent ion and the appearance of each of its fragment ions. Precursor ions may be characterised by their reduction in intensity as fragmentation energy increases. Conversely, fragment ions may be characterised in that their intensity increases with increasing fragmentation energy. This is quite different to conventional MS$^e$ methods, wherein a single collision energy value is used in the high fragmentation mode.

The preferred embodiment still retains the advantages of the conventional technique. For example, spectral data obtained in one or more low fragmentation acquisition periods can be compared to spectral data obtained in one or more high fragmentation acquisition periods. This enables the parent ions detected in the low fragmentation periods to be associated with their corresponding fragment ions that are detected in the high fragmentation periods, enabling a parent ion to be identified. The fragmentation energy may be varied in a cyclical manner, and the low and high fragmentation data in each cycle may be compared.

Precursor and corresponding product ions may be linked by common chromatographic retention time. Alternatively the method described may be applied to only the high energy cycle in an MS$^e$ high/low collision energy cycle. In this mode of operation the high energy data is conventionally taken at a fixed collision energy, which is a compromise to give efficient fragmentation of all the species co-eluting at a particular time. Using the method of the preferred embodiment, multiple spectra at different collision energies are available for each retention time point. In this case, an optimal collision energy range may be chosen for each species present.

According to a preferred embodiment the SFV data from acquisition periods that correspond to high SFV values may be combined over a chromatographic peak. Such data may then be compared to a library of fragment ion spectra so as to identify the ions. For example, an ESI fragmentation based library such as "MsforID" may be used to identify the peaks. Note that "MSfor ID" uses a library where each compound has reference spectra at several (e.g. 10) fragmentation voltages. It may be expected that this would give a good match to non-MS/MS data where the SFV has been varied over a wide range.

The preferred method may use only spectral data from acquisition periods that represent optimised operational parameter values. Reconstructing mass chromatograms from regions of the fragmentation voltage cycle at which parents or daughter ions for each species are optimised can reduce the complexity of fragment ion spectra used in subsequent post-processing.

An embodiment of the present invention will now be described with reference to Table 1. According to a preferred embodiment the SFV is not scanned progressively, but is stepped between a plurality of discrete voltages. The range of SFV voltages over which the SFV is stepped may change as different types of ions pass through the SFV region. When coupled to an upstream separation device, such as a chromatography device, the values of the SFV are preferably selected so as to be at or close to the optimum value of the type of ion that is being subjected to the SFV (if this information is available). A single value of SFV may be close enough to the optimum SFV for a plurality of different types of ions not to affect the sensitivity of their detection significantly. It will therefore be appreciated that it is not necessary to change the range of values of the SFV if such ions are being analysed sequentially. Table 1 below shows an example of such an embodiment.

TABLE 1

| Name | m/z | SFV (optimum) | SFV (selected) | Duty Cycle |
|---|---|---|---|---|
| Compound A | 174 | 25 | 29 | 33 |
| Compound B | 82 | 28 | 29 | 33 |
| Compound C | 233 | 32 | 29 | 33 |
| Compound D | 609 | 33 | 29 | 33 |
| Compound E | 502 | 45 | 48 | 33 |
| Compound F | 296 | 48 | 48 | 33 |
| Compound G | 192 | 48 | 48 | 33 |
| Compound H | 405 | 50 | 48 | 33 |
| Compound I | 303 | 75 | 75 | 33 |
| Compound J | 321 | 75 | 75 | 33 |

According to the embodiment in Table 1, the ions of 10 compounds A-J are analysed. The optimum SFV for each of the types of ions is known. The chromatographic retention time of the compounds is not known and therefore it is not possible to select a single SFV value in order to optimise the SFV value at a particular retention time. In the prior art a single compromise SFV value would need to be used throughout the experiment.

However, in this embodiment of the present invention the SFV is stepped between three different SFV values sequentially and repetitively, namely between 29 V, 48 V and 75 V. As can be seen from Table 1, these SFV values are selected to be at, or close to, the optimum SFV values of the ions passing through the SFV region. The example assumes that a +/−5 V difference between the selected SFV and the optimum SFV does not affect sensitivity significantly. Spectral data from each of the three SFV values is stored at each chromatographic time point. Preferably, the rate of acquisition is selected such that at least 5 to 10 cycles of the three SFV values are recorded over the eluting chromatographic peak. The data acquired during the different selected SFV values may be stored separately and so may be extracted separately in order to provide a mass chromatogram of a particular species that has minimal chemical noise. In this example, one third of the time is spent at each of the three selected SFV values and, as the optimum SFV is within +/−5% of the chosen SFV values, the duty over which each species is at an optimum value is 33%.

According to another preferred embodiment, the ions are also separated by liquid chromatography and the SFV is stepped repetitively and sequentially between a plurality of discrete voltages as different types of ions elute from the LC column and pass through the SFV region. In this embodiment it is known that compounds eluting at a particular retention time range will have a particular optimum SFV value. However, the precise retention time for each compound is not known. According to conventional methods, a single compromise SFV value would need to be chosen for each RT range. However, according to this embodiment of the present invention, the SFV is stepped repetitively and sequentially between a plurality of discrete voltages for each of at least some of the retention time ranges. The values of the SFV voltages for each retention time range are preferably selected so that at least one of the voltages is at or close to the optimum value of the type of ion that is expected to elute in the retention time range.

The different compounds are separated by the LC column and pass through the SFV region in an order according to their elution time. The SFV may then be stepped repetitively and sequentially between different values which change as a function of the elution time from the LC column such that the ions passing through the SFV region are subjected to SFV values which are at, or close to, the optimum SFV for at least some of the ions passing through the SFV region at that retention time.

Table 2 below shows an example of such an embodiment, wherein the same compounds as shown in Table 1 were analysed. The optimum SFV for each of the types of ions is known. However, the elution time of each type of ion is known only to +/−0.1 minute. The ions are arranged to pass through the SFV region in order of increasing elution time from the LC column. As the ions pass through the SFV region, the SFV is stepped between three different SFV values, namely 29 V, 48 V and 75 V. As can be seen from Table 2, these SFV values are selected to be at, or close to, the optimum SFV values of the ions expected to be passing through the SFV region.

TABLE 2

| Name | Elution time (±0.1) | m/z | SFV (optimum) | SFV (selected) | Duty Cycle |
|---|---|---|---|---|---|
| Compound A | 0.5 | 174 | 25 | 29 | 50 |
| Compound C | 0.5 | 233 | 32 | 29 | 50 |
| Compound G | 0.6 | 192 | 48 | 48 | 50 |
| Compound F | 0.8 | 296 | 48 | 48 | 50 |
| Compound B | 0.9 | 82 | 28 | 29 | 33 |
| Compound J | 1.0 | 321 | 75 | 75 | 50 |
| Compound E | 1.4 | 502 | 45 | 48 | 50 |
| Compound D | 1.5 | 609 | 33 | 29 | 50 |
| Compound I | 1.8 | 303 | 75 | 75 | 100 |
| Compound H | 2.0 | 405 | 50 | 48 | 100 |

During the retention time range of 0.0-0.5 minutes the SFV value is set to 29 V. As can be seen from Table 2, during the retention time range of 0.5-0.6 minutes the SFV value is repeatedly alternated between 29 V and 48 V, giving a 50% duty cycle for compounds A, C and G. About the retention time of 0.8 minutes the SFV value is repeatedly alternated between 48 V and 29 V, giving a 50% duty cycle for compounds F and B. About the retention time of 0.9 minutes the SFV value is repeatedly alternated between 48 V, 29 V and 75 V, giving a 33% duty cycle for compounds F, B and J. During the retention time range of 1.4-1.5 minutes the SFV value is repeatedly alternated between 48 V and 29 V, giving a 50% duty cycle for compounds E and D. At a retention time of 1.8 minutes a single SFV value of 75 V is used, giving a 100% duty cycle for compound I. At a retention time of 2 minutes a single SFV value of 48 V is used, giving a 100% duty cycle for compound H.

The example of Table 2 assumes that a +/−5 V difference between the selected SFV and the optimum SFV does not affect sensitivity significantly. The example also assumes that the SFV will be profiled to be optimum for any compounds eluting within 0.1 minute of the stated elution time. The end result is a duty cycle that varies between 33% and 100%. The data acquired during the different selected SFV values may be stored separately and so may be extracted separately in order to provide a chromatogram that has minimal chemical noise.

Although the preferred embodiments of the present invention have been described above in terms of varying the SFV, it is contemplated that alternative operational parameters of the spectrometer may be varied instead.

In mass spectrometry it is sometimes required to control an operational parameter of the instrument in order to optimise the acquisition of data from species of interest. However, it is often not possible to determine the optimal acquisition parameters for the species of interest in advance of an experiment. Also, different parameters may be optimal for different species of interest.

It is known to analyse ions and accumulate data whilst the value of an operational parameter, such as collision energy, is being ramped. This enables the operational parameter to be optimised for each of the species during a part of the acquisition period and hence the data obtained can be used to generate a spectrum having contributions from optimal values for each species. However, the operational parameter will not be optimised for any given species during most of the acquisition period and hence the spectrum necessarily includes significant contributions from non-optimal values.

The operational parameter may be the collision energy in an LC-MSMS experiment designed to quantify a target analyte in a complex mixture. In such an experiment a quadrupole mass filter is used to selectively transmit a m/z range containing the target analyte ion to a downstream fragmentation region. The transmitted ions are then fragmented and the resulting fragment ions analysed in order to identify the target analyte. However, other co-eluting analytes or background ions may be present in the m/z range transmitted by the mass filter. These other ions can yield fragments with identical or similar m/z to the fragment ions of the target analyte, but sometimes at different collision energies. If the collision energy is ramped during the experiment and the acquired data integrated across the ramping time, these fragment ions can interfere with the signals for the fragment ions of the target analyte, thus reducing or destroying the quantitative fidelity, mass accuracy of ion mobility accuracy of the experiment.

However, according to a preferred embodiment of the present invention, data is acquired and stored separately and so an optimal collision energy range can be selected for one or more of the analytes in the transmitted m/z range. This may be used to improve the purity of the measurement of mass, mobility or intensity, or indeed any other quantity that can be determined by the experiment in question such as a peak width, retention time or isotope ratio.

Another example relates to detection systems in spectrometers that have a finite dynamic range. Often in complex mixtures to be analysed, species with very different abundances are introduced into the spectrometer at the same time. It is known to attenuate the ion beam so as to counteract the high abundance of certain species. Discrete transmission values may be provides for different species, for example, by using a DRE lens. Typically, only two or three attenuation values are chosen and a single transmission value is chosen for each species. However, in this approach it is likely that most of the signal will be discarded for some species.

In a preferred embodiment of the present invention, the transmission value may be ramped continuously in a predetermined cycle according to a function R(t), and an optimal transmission range (t1,t2) may be chosen for each species s of interest leading to an integrated measured signal Ds where $$D_s \int_{t_1}^{t_2} dt\, d_s(t)$$

where ds(t) is the signal measured over the ramp as a function of time.

The data may then be rescaled to compensate for the truncation in time to produce a value D's that may be used quantitatively:

$$D'_s = D_s \frac{\int_0^{t_{max}} dt R(t)}{\int_{t_1}^{t_2} dt R(t)}$$

As before, mass and/or mobility measurements would be obtained from datasets integrated over the optimal range for each species. With an appropriate choice of ramp R(t), optimal data can be obtained for a wider range of species than is possible when a limited number of attenuation steps are used.

Figure 6:
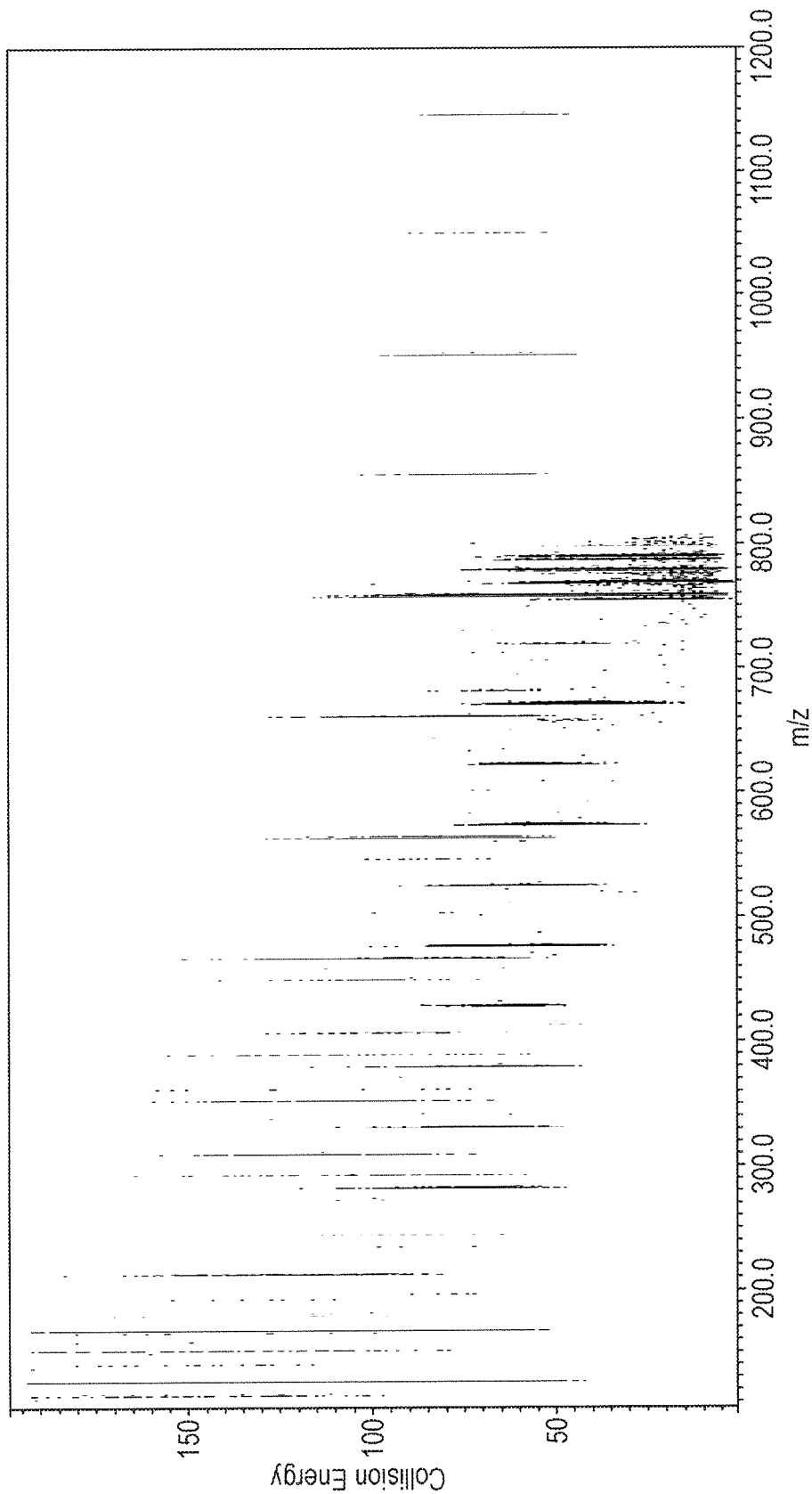
FIG. 6 shows a plot illustrating that different fragment ions of a parent ion may appear and disappear at different collision energies.

FIGS. 6 and 7 show an example of the invention in which data was obtained by selecting a doubly charged precursor ion of Glu Fibrinopeptide m/z=785.8 using a quadrupole mass filter and subjecting it to a range of collision energies in a RF confined collision cell. The collision energy was ramped linearly over the range from 0 eV to 80 eV during a 2 second cycle time. Two hundred individual mass spectra were acquired over this cycle time. A total of 14 such cycles were recorded and spectra from each cycle corresponding to the same collision energy were combined so as to give a single two dimensional data set of collision energy and mass to charge ratio.

FIG. 6 shows a plot of acquisition number verses s m/z where 0-200 acquisitions correspond to 0-80 eV collision energy. It is clear that different fragment ions appear and disappear at different collision energies. This 'heat map' may be used as a 2D fingerprint for this compound and allows recognition of this compound using a database, even in a complex mixture of compounds. The appearance of different fragment ions at different collision energies is indicative of the chemical bond energies and the electronic structure of the precursor ion. It also provides information about the fragmentation pathways for this ion. In addition, by selecting regions of the 2D data, mass spectra corresponding to the optimum collision energy for the maximum sensitivity of each fragment may be selected.

Figure 7A:
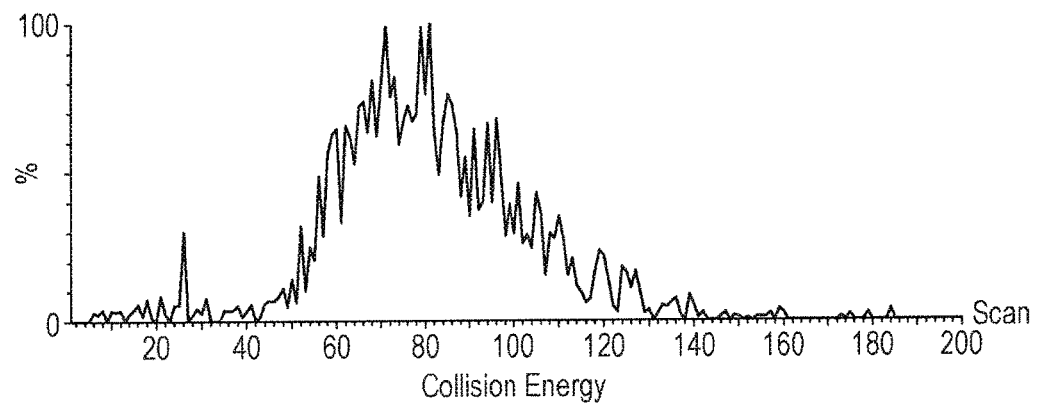
FIGS. 7A and 7B show reconstructed mass, collision energy plots for different fragment ions
Figure 7B:
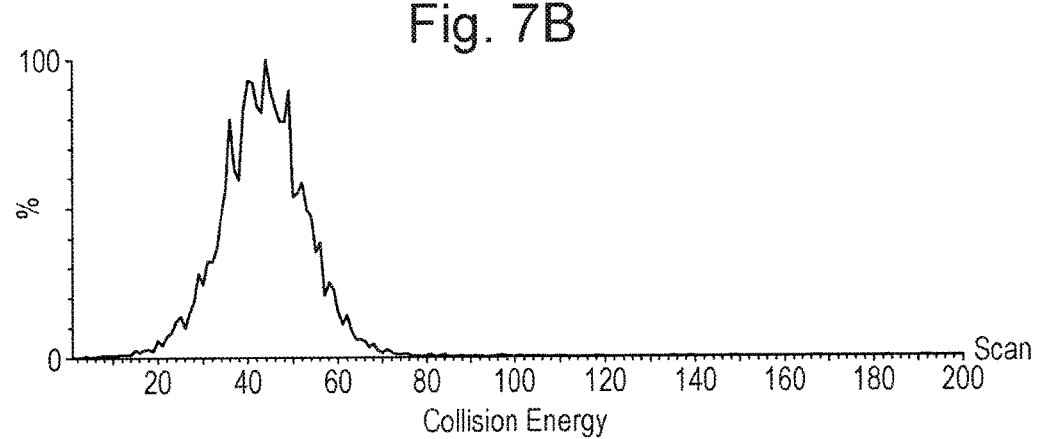
Figure 7C:
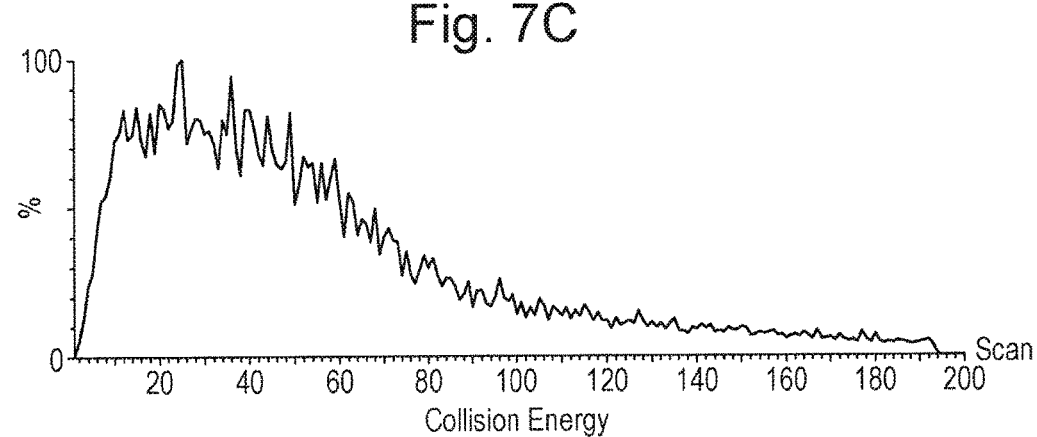
FIG. 7C shows the total ion current verses collision energy for the entire mass range.

FIG. 7A shows a reconstructed mass, collision energy plot for the singly charged fragment ion m/z 660. FIG. 7B shows a reconstructed mass, collision energy plot for the doubly charged fragment ion m/z 670. FIG. 7C shows the total ion current verses collision energy for the entire mass range. It is clear that the range of collision energies and the optimum collision energy is different for these two fragment ions. In the prior art a compromise single collision energy value would be chosen for all fragment ions which would clearly be non-optimum for many species.

Figure 8A:
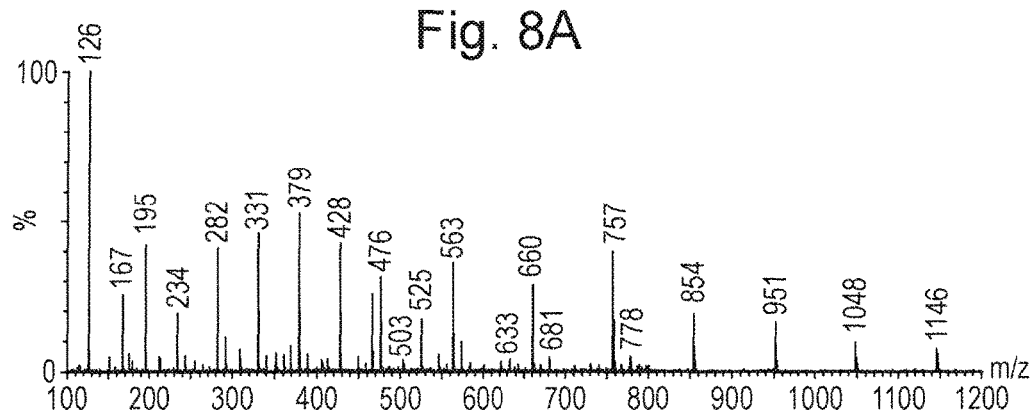
FIG. 8A shows the mass spectrum at the apex of the peak in FIG. 7A.
Figure 8B:
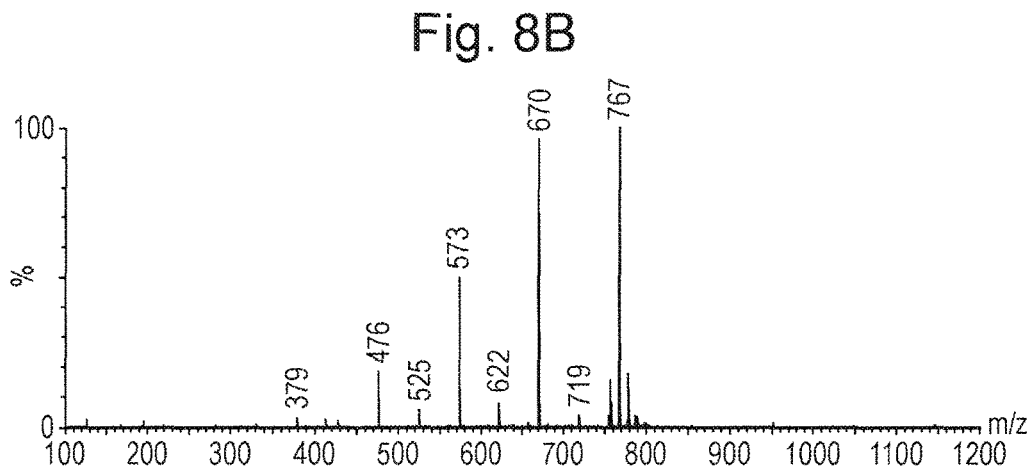
FIG. 8B shows the mass spectrum at the apex of the peak in FIG. 7B.
Figure 8C:
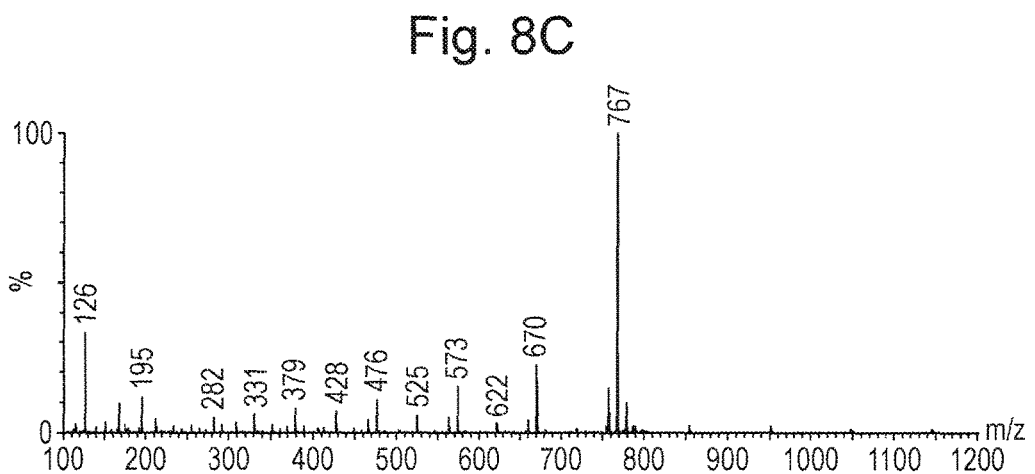
FIG. 8C shows the mass spectrum obtained by summing all the spectra over all the entire collision energy range.

FIG. 8A shows the mass spectrum at the apex of the peak in FIG. 7A. FIG. 8B shows the mass spectrum at the apex of the peak in FIG. 7B. FIG. 8C shows the mass spectrum obtained by summing all the spectra over all the entire collision energy range.

Although the present invention has been described with reference to preferred embodiments, it will be understood by those skilled in the art that various changes in form and detail may be made without departing from the scope of the invention as set forth in the accompanying claims.

The invention claimed is:

1. A method of mass spectrometry or ion mobility spectrometry comprising:
   providing a plurality of species of ions to a spectrometer;
   analysing the ions during a plurality of sequential acquisition periods so as to obtain spectral data relating to the ions;
   varying, by a controller, the value of an operational parameter of the spectrometer such that it has different values during different ones of said acquisition periods, wherein the spectral data obtained for a given ion varies depending on the value of the operational parameter;
   storing, by the controller, the spectral data obtained during the said different acquisition periods separately;
   selecting or identifying a target ion;
   interrogating, by the controller, the spectral data obtained during said different acquisition periods so as to identify a first set of said acquisition periods that include data corresponding to said target ion; and
   selecting, by the controller, spectral data obtained in only a subset of said first acquisition periods so as to obtain spectral data that is optimised for said target ion,
   wherein said plurality of species of ions are provided from a sample and the spectral data obtained in said subset of said first acquisition periods is used to identify or quantify an analyte in the sample, or an analyte derived from said sample.

2. The method of claim 1, wherein the sequential acquisition periods are performed on the same sample in a single experimental run; and/or are performed immediately one after the other.

3. The method of claim 1, comprising separating a plurality of molecular analytes according to a physicochemical property in a separator such that each analyte elutes from the separator over a respective elution time period, wherein said analytes are then ionised so as to form said plurality of species of ions, and wherein a plurality of said acquisition periods are performed during the elution time period for each analyte such that ions of, or derived from, each analyte are analysed in a plurality of said acquisition periods; or
   comprising separating said plurality of species of ions according to a physicochemical property in a separator such that each species elutes from the separator over a respective elution time period, and performing a plurality of said acquisition periods during the elution time period for each species such that ions of, or derived from, each species of ion are analysed in a plurality of said acquisition periods.

4. The method of claim 3, comprising varying the value of the operational parameter in a cyclical manner and for a plurality of cycles during each analyte elution time period, wherein the value of the operational parameter is varied as a function of time in the same manner or pattern for each of the cycles, and wherein y cycles are performed during the elution time period for each analyte; wherein y is selected from the group consisting of: ≥2; ≥3; ≥4; ≥5; ≥6; ≥7; ≥8; ≥9; ≥10; ≥15; ≥20.

5. The method of claim 4, wherein said subset of first acquisition periods corresponds to acquisition periods in said plurality of cycles that have the same or different operational parameter values, or range of values.

6. The method of claim 1, wherein the target ion has a known physicochemical property value, and said step of interrogating the spectral data so as to identify the set of first acquisition periods comprises interrogating the spectral data so as to identify a set of first acquisition periods that includes data corresponding to ions having said known physicochemical property value.

7. The method of claim 1, comprising continuously scanning the value of the operational parameter across different values during the acquisition periods; or
comprising discontinuously stepping the value of the operational parameter between different values for the different acquisition periods.

8. The method of claim 1, comprising varying the value of the operational parameter in a cyclical manner, wherein the value of the operational parameter is varied as a function of time in the same manner or pattern for each of the cycles.

9. The method of claim 8, wherein said set of first acquisition periods includes one or more acquisition periods from each of a plurality of different ones of said cycles.

10. The method of claim 1, wherein ions of the same ion species are analysed in a plurality of different ones of said acquisition periods such that different spectral data is obtained for said same ion species in the different acquisition periods.

11. The method of claim 1, wherein a plurality of species of ions are analysed during each of a plurality of the acquisition periods.

12. The method of claim 1, comprising combining/integrating, summing or averaging spectral data obtained in said first subset of acquisition periods to form one or more combined, summed or averaged data set.

13. The method of claim 12, comprising only combining/integrating, summing or averaging spectral data obtained in different acquisition periods that correspond to the same operational parameter value or that correspond to the same range of operational parameter values.

14. The method of claim 1, wherein said step of selecting spectral data obtained in only a subset of said first acquisition periods so as to obtain spectral data that is optimised for said target ion comprises: selecting spectral data from acquisition periods of said first set that have higher signal to noise ratios, and discarding or ignoring spectral data in the other acquisition periods of said first set that have lower signal to noise ratios; and/or selecting spectral data from acquisition periods of said first set that have higher signal intensity, and discarding or ignoring spectral data in the other acquisition periods of said first set that have lower signal intensity.

15. The method of claim 1, wherein the step of providing the plurality of species of ions comprises providing said plurality of species of ions separated according to a physicochemical property; the method comprising repeatedly varying the operational parameter between at least two values such that each of the different separated species of ions is subjected to said at least two operational parameter values, and wherein the acquisition periods are selected such that spectral data obtained at each of said at least two values is recorded separately.

16. The method of claim 15, wherein the optimum parameter value is known or predetermined for at least two of the species of ions, and wherein said at least two operational parameter values are substantially the optimum parameter values for said at least two species such that each species will be subjected to an operational parameter value that is substantially at its optimum value during at least some of the acquisition periods; or comprising repeatedly cycling the operational parameter value between different values, wherein each cycle comprises at least two different values, and wherein the values of the operational parameter in the cycles are varied as a function of the physicochemical property values of the species being subjected to the operational parameter.

17. The method of claim 1, wherein the operational parameter value that is varied is selected from one of:
a potential difference used to accelerate the ions;
a collision energy with which the ions are caused to collide with a gas or surface;
a fragmentation energy for fragmenting the ions;
a gain of a detector for detecting the ions;
an ion beam attenuation;
a reaction time with which the ions are reacted with reactants;
an amount of attenuation or filtering of the ions; and
a source ionisation efficiency or sensitivity or ionisation energy.

18. A method of mass spectrometry or ion mobility spectrometry comprising:
providing a plurality of species of ions to a spectrometer;
analysing the ions during a plurality of sequential acquisition periods so as to obtain spectral data relating to the ions;
varying, by a controller, the value of an operational parameter of the spectrometer such that it has different values during different ones of said acquisition periods, wherein the spectral data obtained for a given ion varies depending on the value of the operational parameter;
associating, by the controller, the spectral data obtained in each said acquisition period with its respective operational parameter value(s) so as to form associated data for each said acquisition period;
providing, by the controller, a database of analytes, wherein for each analyte the database includes spectral data obtained at a plurality of said operational parameter values, wherein the spectral data is associated with the operational parameter value(s) that it was obtained at;
searching, by the controller, said database using said associated data; and
determining, by the controller, an analyte in the database that has spectral data at a plurality of operational parameter values which matches the associated data obtained at substantially the same operational parameter values.

19. A mass or ion mobility spectrometer comprising:
an ion analyser configured to analyse ions during a plurality of sequential acquisition periods so as to obtain spectral data relating to the ions; and
a controller configured to:
vary the value of an operational parameter of the spectrometer such that it has different values during the different acquisition periods and such that the spectral data obtained for a given ion varies depending on the value of the operational parameter;
store the spectral data obtained during the different acquisition periods separately;
interrogate the spectral data obtained during the different acquisition periods so as to identify a first set of first said acquisition periods that include data corresponding to a selected target ion; and
select spectral data obtained in only a subset of said first acquisition periods so as to obtain spectral data that is optimised for said target ion.

* * * * *